United States Patent [19]

Heckele et al.

[11] Patent Number: 5,309,894
[45] Date of Patent: May 10, 1994

[54] ENDOSCOPE FOR INTRODUCTION INTO A HOLLOW ORGAN OF A LIVING THING

[75] Inventors: Helmut Heckele, Knittlingen; Rudolf Heimberger, Oberderdingen, both of Fed. Rep. of Germany

[73] Assignee: Richard Wolf GmbH, Knittlingen, Fed. Rep. of Germany

[21] Appl. No.: 923,697

[22] Filed: Jul. 31, 1992

[30] Foreign Application Priority Data

Aug. 3, 1991 [DE] Fed. Rep. of Germany ....... 4125806

[51] Int. Cl.$^5$ .............................................. A61B 1/00
[52] U.S. Cl. .......................................... 128/4; 128/20; 606/198
[58] Field of Search ............................ 128/20, 3, 4, 6, 7, 128/8, 10, 11, 17, 18; 606/198, 191; 604/104, 105, 106, 107, 108, 109

[56] References Cited

U.S. PATENT DOCUMENTS

| | | | |
|---|---|---|---|
| 3,570,498 | 3/1971 | Weighton | 604/109 |
| 3,717,151 | 3/1971 | Collett. | |
| 3,866,599 | 2/1975 | Johnson | 128/6 X |
| 3,994,301 | 11/1976 | Agris | 606/190 |
| 4,016,867 | 4/1977 | King et al. | |
| 4,027,510 | 6/1977 | Hiltebrandt | 128/6 X |
| 4,168,709 | 9/1979 | Bentov | 606/198 |
| 4,471,766 | 9/1984 | Terayama | 128/6 |
| 4,608,965 | 9/1986 | Anspach et al. | |
| 4,791,913 | 12/1988 | Maloney | 128/6 |
| 5,002,560 | 3/1991 | Machold et al. | 606/198 |
| 5,113,846 | 5/1992 | Hiltebrandt et al. | 128/20 |
| 5,160,341 | 11/1992 | Brenneman et al. | 606/198 |
| 5,183,033 | 2/1993 | Wilk | 128/20 |
| 5,197,971 | 3/1993 | Bonutti | 604/105 X |

FOREIGN PATENT DOCUMENTS

| | | | |
|---|---|---|---|
| 640126 | 12/1936 | Fed. Rep. of Germany | 604/106 |
| 2318860 | 1/1978 | Fed. Rep. of Germany. | |
| 8303342 | 7/1983 | Fed. Rep. of Germany. | |
| 3330921 | 2/1985 | Fed. Rep. of Germany. | |
| 4125806 | 6/1993 | Fed. Rep. of Germany. | |
| 1173194 | 12/1969 | United Kingdom. | |

Primary Examiner—Richard J. Apley
Assistant Examiner—Karen A. Jalbert
Attorney, Agent, or Firm—Panitch Schwarze Jacobs & Nadel

[57] ABSTRACT

The endoscope for introduction into a hollow organ of a living thing makes it possible for the hollow organ to be pulled against a more solid outer structure and to fix it thereto for the duration of the treatment. The endoscope is therefore provided with a retaining device, which can be used in the outer shaft of the endoscope and is guided therein, and has a plurality of hook elements, on the distal end of which hooks are formed by pushing out from the distal end of the outer shaft as a result of spreading, and with a stop disc which can be adjusted on the outer shaft. Spreading of the hook element ends can be controlled optically. After spreading the hook element ends, the endoscope is drawn back until it rests on the hollow organ in order to fix the hollow organ and secured in this position by means of the stop disc. A measuring scale, which enables direct reading of the spread position of the hook element ends at the moment of contact with the tissue wall of the hollow organ, is provided to measure the hollow organ.

14 Claims, 2 Drawing Sheets

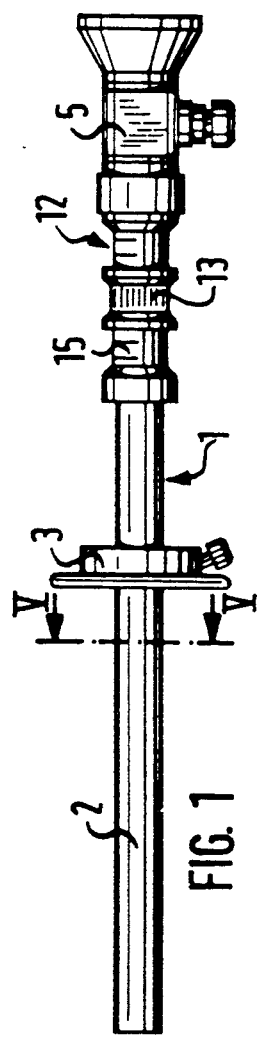
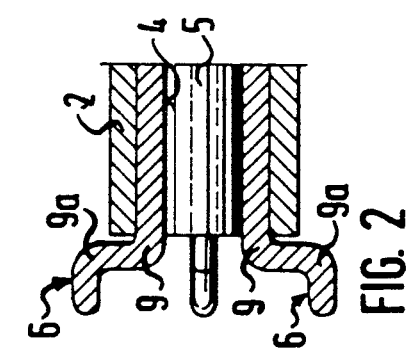
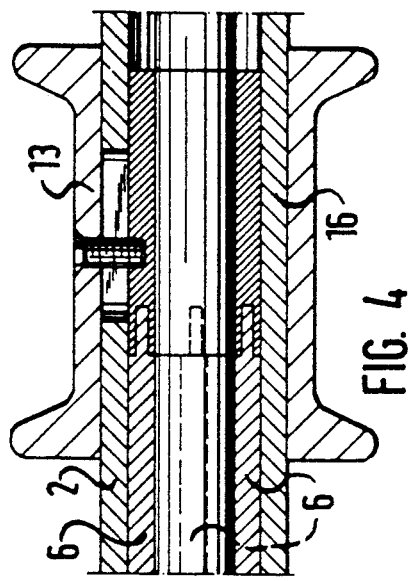
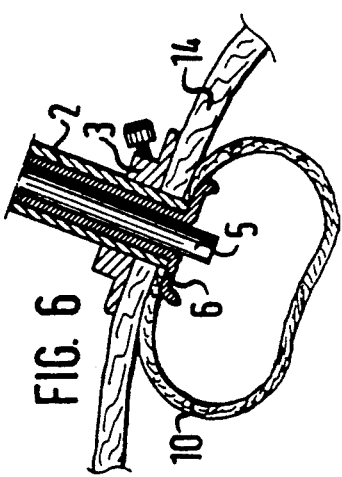
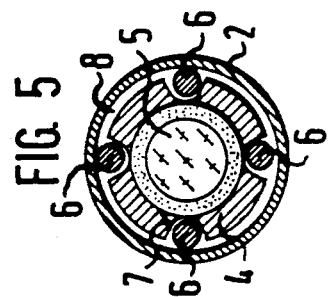
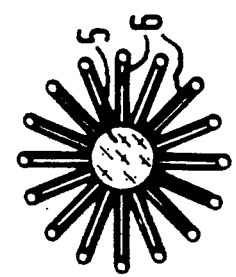

ENDOSCOPE FOR INTRODUCTION INTO A HOLLOW ORGAN OF A LIVING THING

BACKGROUND OF THE INVENTION a) Field of the Invention

The invention relates to an endoscope for introduction into a hollow organ of a living thing, the endoscope comprising a hollow outer shaft and an optical system arranged therein.

b) Description of the Prior Art

Endoscopy of the interior of hollow organs of humans and animals is often made difficult due to the fact that the hollow organs easily evade the observation instrument because of their great flexibility. It is often not possible to achieve sufficient distance between endoscope optical systems and the region of the hollow organ to be investigated because of this great flexibility, so that it is not possible to achieve a sharp picture. This also means that there is hardly any space to operate instruments. Furthermore, it is often necessary, for example when there are pathological changes in the hollow organs, to measure the space which still remains, for example for tubular organs the free passage, in order to be able to carry out appropriate treatment measures.

A hysteroscope, which is designed to expand the uterus with gas and then to maintain this state with the aid of mechanically operating spreading elements and to be able to allow the gas to escape, is known from German Patentschrift 2 318 860. This hysteroscope essentially comprises an adapter serving to seal the uterus, an instrument shaft, through which an optical system can be introduced and which has a gas connection. Spreading elements, which can be brought to rest against wall regions of the uterus, are provided at the distal end of the endoscope to maintain the spread state. The arrangement and shape of the spreading elements thus determine the extent to which the uterus can be kept clear. A certain stabilisation of the tissue can thus be achieved, but no fixing of the hollow organ in the real sense.

Finally, a device for use in connection with catheters, for example for wound drainage, is known from U.S. Pat. No. 3,717,151, by means of which the object of being able to arrange this device in the interior of the body of a living thing is to be fulfilled, such that the device once positioned cannot be released accidentally. The device therefore essentially comprises two coaxially arranged sleeves which can be displaced relative to one another and gripping fingers which can be driven out of the distal end of the outer sleeve, and a fixing collar which can be displaced on the outer sleeve. After introducing this device into a wound or into a body cavity, for example the stomach of a cow, the gripping fingers are driven out of the distal end. The gripping fingers are thus spread outwards in the radial direction and are placed, in this example, against the stomach wall. The fixing collar on the outer sleeve is then pushed towards the distal end until it contacts, for example the skin, and is fixed there. The whole of the device is thus secured against falling out of the body and/or falling into the body cavity accidentally. A reference to use for fixing hollow organs is not to be found in this specification.

As far as measuring hollow organs is concerned, reference may be made to German Patentschrift 3 330 921, which describes a probe without an optical system to determine the size of the interior of hollow organs, in particular the uterine cavity. In this instrument, two sensors which can be spread apart from one another and are provided on the distal end of the probe are spread open by axially displacing a rod-like transfer member until it contacts the inner wall of the hollow organ. An indicator, for example a dial gauge, from which the measured result can be read, is arranged on the proximal end of this probe. This device is also not able to avoid the evasive movement of the hollow organ to be treated during treatment.

It is therefore the object of the invention to improve an endoscope of the type mentioned in the introduction, so that it is possible to pull hollow organs against an outer, more solid structure and to be able to fix them thereto, for examining, measuring and treating such hollow organs of living things.

SUMMARY OF THE INVENTION

This object is achieved by means of a retaining device which can be guided in the outer shaft and has a number of resiliently deformable hook elements which can be moved in and out of the outer shaft at the distal end, by stop means arranged on the outer shaft to be adjustable and fixable, by an adjusting device provided in the proximal region of the outer shaft for displacing the retaining device in the outer shaft and by an indicator to control the position of the adjusting device.

A hollow organ to be treated can be effectively fixed by means of this endoscope using optical control. Furthermore, for example the remaining cross-section of a pathologically changed tubular hollow organ can be determined using the same endoscope, in that the spreading path of the hook elements can be read until they rest against the organ wall in a manner which can be controlled optically. There is also more space available now for using the treatment instruments.

It is preferred that the hook elements each consist of a relatively long, highly resilient wire having a distal, resiliently deformable and automatically spreadable hook part.

Advantageously, the hook part, produced by bending, of each hook element has a further resiliently deformable backward bend extending counter to the first forward bend at its distal end.

An inner shaft accommodating the optical system may be provided in an annulus between the optical system and the outer shaft. Suitably, the hook elements are accommodated in recesses on the inner shaft.

Preferably, the hook elements are attached at their proximal end to a displaceable sleeve in the annulus between the outer shaft and the optical system, and the adjusting device for the hook elements comprises a sliding sleeve guided on the proximal side of the outer shaft and which is connected to the sleeve supporting the hook elements by means of a rigid connecting member.

The indicator suitably comprises a measuring scale provided on the outer shaft.

Features to be emphasized include:
- the design of the hook elements from a highly resilient wire or tape, which structure tolerates a high degree of reverse bending;
- the atraumatic behaviour of the hook elements, which can be achieved by bending back the distal ends of the hook elements, on contact with the organ wall; and the measuring scale in the region of the adjusting device, the graduation of which is preferably proportional to the spreading path of the hook elements and hence gives direct information on the particular position of the same.

In another aspect, the invention may be expressed as an endoscope for introduction into a hollow organ of a living thing, comprising a hollow outer shaft and an optical system arranged therein, characterised in that a plurality of rigid, L-shaped hook elements are linked to be radially pivotable at the distal end of the outer shaft, in that an axially movable inner shaft, which accommodates the optical system and is guided on the outer shaft, is provided to pivot the hook elements, in that stop means are arranged to be adjustable and fixable on the outer shaft, in that an adjusting device provided in the proximal region of the outer shaft is provided for displacing the inner shaft, and in that an indicator is provided to control the position of the adjusting device.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

FIG. 1 shows a first endoscope in side view.

FIG. 2 shows the distal end of the endoscope according to FIG. 1 with pushed-out hook elements, shown in longitudinal section.

FIG. 3 shows an end view of the distal end of the endoscope with pushed-out hook elements.

FIG. 4 shows an axial section through the proximal end of the endoscope.

FIG. 5 shows a cross-section through the endoscope along line V—V in FIG. 1.

FIG. 6 shows the endoscope in use, represented schematically.

DESCRIPTION OF THE PREFERRED EMBODIMENTS

Figure 8:
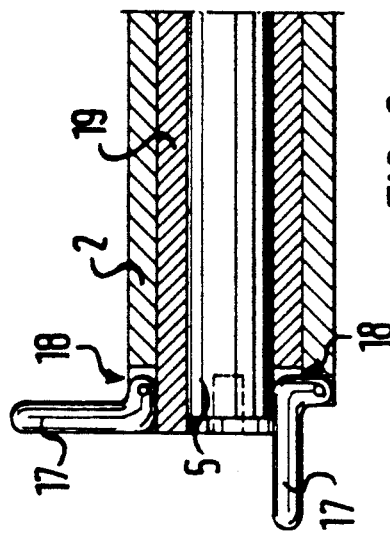
FIGS. 8 and 9 show further embodiments of the endoscope in partial and axial section.

According to FIGS. 1, 2 and 5, the endoscope 1 essentially comprises an outer shaft 2 having a stop disc 3 attached displaceably thereon, an inner shaft 4 and an optical system 5 which can be introduced into the inner shaft 4.

In accordance with FIGS. 2 and 5, a plurality of hook elements 6 are arranged and axially guided in an annulus 8 between the outer shaft 2 and the optical system 5. Guiding may take place along longitudinal grooves 7 in the outer surface of the inner shaft 4 or by means of a guide ring provided with corresponding recesses. The hook elements 6 consist of a relatively long, highly resilient wire or tape and have in the region of their distal end an immanent forward bend 9, which extends beyond the distal end of the outer shaft 2, as shown in FIG. 2, in a radial direction above the outer shaft 2 when the hook element is pushed out, and thus acts as a hook part. In order to make certain of avoiding a traumatic effect, the forward-bend end of each hook element 6 is provided at its distal end with a further immanent backward bend 9a extending counter to the forward bend mentioned. The length of the hook elements 6 is selected so that they can be completely drawn into the outer shaft 2 of the instrument 1, which results in the avoidance of a living thing experiencing additional trauma due to the hook elements 6 when the endoscope 1 is introduced into a hollow organ 10 or 11. According to FIG. 4, the hook elements 6 are fixed at their proximal end to a sleeve 16 displaceable in the annulus 8 between the outer shaft 2 and the optical system 5. The sleeve 16 is connected to an adjusting device 13 in the form of a sliding sleeve in the region of the handle 12 of the instrument 1 by means of a connecting screw.

The mode of operation of this embodiment of the endoscope is as follows:

To treat a hollow organ 10, for example that according to FIG. 6, the endoscope 1 with its outer shaft 2 is initially introduced into this hollow organ, wherein the hook elements 6 are drawn into the outer shaft 2. After introduction, the sliding sleeve 13 on the handle 12 of the endoscope 1 is pushed forward in the distal direction, this effects pushing out of the immanent hook parts 9 over the distal end of the outer shaft 2. This progressively raises the external support of the hook parts 9, so that they open increasingly and act as hooks. They thus finally reach the inner wall of the hollow organ 10, against which they rest. In this position the endoscope 1 together with the hollow organ 10 is pulled back against a more solid tissue structure, for example against the abdominal wall 14, until it rests on it and then the stop disc 3 is pushed as far as the outside of this more solid tissue structure and fixed in the stop position.

The hollow organ 10 is thus securely fixed and can be precisely investigated and treated endoscopically.

Figure 7:
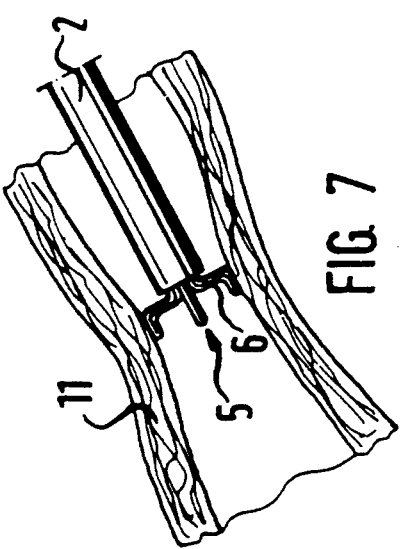
FIG. 7 also shows a schematic representation of the use of the endoscope as a measuring instrument.

In order to be able to carry out measurements in hollow organs using the endoscope 1, a measuring scale 15, on which the measurement corresponding to the distance of the ends from opposing hook parts 9 can be read, is provided in the region of the proximal handle 12. For tubular hollow organs 11 (FIG. 7), the endoscope 1 is introduced to the region of interest with the aid of control by means of the optical system 5 and then the immanent hook parts 9 are pushed out of the distal end of the outer shaft 2 until they contact the wall of the hollow organ 11. The free passage of a tubular hollow organ which still remains can thus be measured, for example in the case of pathological changes.

In the modified embodiment according to FIG. 8, the proposed endoscope may also be designed with respect to the hook elements, so that a plurality of rigid, L-shaped hook elements 17 are distributed on the periphery in axial slots 18 at the distal end of the outer shaft 2 and linked to be radially pivotable, as shown in FIG. 8. The linking and the design of the hook elements 17 is thus selected so that the hook elements do not project radially outwards with respect to the outer shaft 2 with the aid of the optical system 5 in their non-operating position, as shown in the lower half of FIG. 8. The upper half of FIG. 8 shows the operating position of the hook elements 17. The hook elements are pivoted by axial forward movement of the inner shaft 19 in the outer shaft 2, wherein the inner shaft, also accommodating the optical system 5, initially presses against the bend of the L-shaped hook elements in order to pivot these elements radially outwards, as can be seen at the bottom of FIG. 8, and then the other limb of the hook elements remains pivoted radially outwards due to its pushed-forward position, as shown at the top of FIG. 8.

Figure 10:
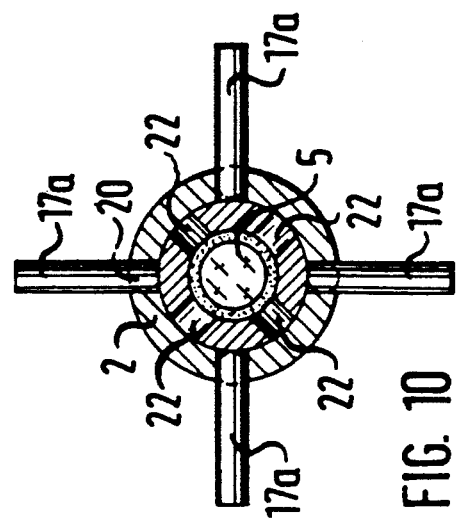
FIG. 10 shows an end view of the representation according to FIG. 9.
Figure 9:
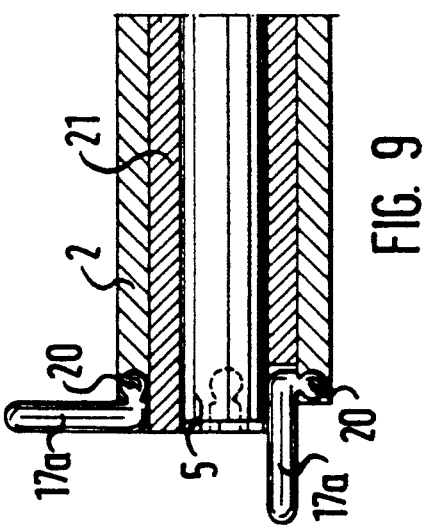

In the further exemplary embodiment according to FIGS. 9 and 10, the inner shaft 21 has a number of recesses 22 corresponding to the number of hook elements 17a mounted in the outer shaft 2 by means of ball and socket joints 20, which recesses 22 serve to fix the hook elements 17a in axis-parallel position, as shown in the lower part of FIG. 9, by means of the optical system 5.

To pivot the hook elements 17a, for example into the position, as shown in the upper part of FIG. 9, the optical system 5 and the inner shaft 21 are initially drawn back in the proximal direction so far that the distal end of the inner shaft 21 lies completely on the proximal side of the proximal end of the hook 17a. The inner shaft 21 is then rotated so that the recesses 22, as shown in FIG. 10, no longer point in the direction of the hook elements 17a. By pushing the inner shaft 21 forward in the direction of the hook elements 17a, the latter are pivoted out in the radial direction by the shaft 21.

To return the hook elements 17a into the axis-parallel rest position, the inner shaft is rotated again until the positions of the hook elements 17a linked in the outer shaft 2 and the recesses 22 of the inner shaft 21 cover each other, so that the hook elements fall back into the rest position, for example when the instrument is pulled out of the body cavity.

So as not to cause any unnecessary trauma when introducing the endoscope into a body cavity, the hook elements 17a in this embodiment also are fixed in their rest position simply by pushing the optical system 5 forward in the distal direction.

The endoscope of the invention 1 may also be designed as a flexible instrument with flexible shafts 2, 4 or 19, 21 instead of rigid shafts, and with a flexible optical system instead of a rigid optical system 5.

The present invention may be embodied in other specific forms without departing from the spirit or essential attributes thereof and, accordingly, reference should be made to the appended claims rather than to the foregoing specification as indicating the scope of the invention.

We claim:

1. Endoscope for introduction through a body structure and into a hollow organ of a living thing, comprising a hollow outer shaft having a proximal region and a distal end, an optical system arranged in the shaft, retaining means guided in the outer shaft and having a plurality of resiliently deformable hook elements which can be moved by said retaining means in and out of the shaft at the distal end, adjustable and fixable stop means arranged on the outer shaft, adjusting means provided in the proximal region of the outer shaft for displacing the retaining means in the outer shaft, and indicator means for reading the position of the adjusting means, each of said deformable hook elements having an immanent bend and a major arm extending distally of said bend, said bend causing said major arm to extend radially outwardly from said shaft when said hook elements are moved out of the shaft at the distal end, such that said major arms when fully extended cooperate with said stop means to pull and hold a hollow organ against a body structure between said arms and said stop means.

2. Endoscope according to claim 1, wherein the hook elements each comprise an elongated, highly resilient wire having a distal, resiliently deformable and automatically spreadable hook part.

3. Endoscope according to claim 2, wherein the hook part of each hook element has a first bend and a further resiliently deformable bend extending counter to the first forward bend at its distal end.

4. Endoscope according to claim 1, further comprising an inner shaft accommodating the optical system in an annulus between the optical system and the outer shaft, and wherein the hook elements are accommodated in recesses on the inner shaft.

5. Endoscope according to claim 4, further comprising a displaceable sleeve in the annulus between the outer shaft and the optical system, said hook elements being attached at one end to said displaceable sleeve, and said adjusting means comprising a sliding sleeve which is guided in the proximal region of the outer shaft and a rigid member for connecting said sliding sleeve to said displaceable sleeve.

6. Endoscope according to claim 1, wherein the indicator means comprises a measuring scale provided on the outer shaft.

7. Endoscope according to claim 1 wherein said major arms, when fully extended, extend substantially perpendicular to the longitudinal axis of said shaft.

8. Endoscope according to claim 1 wherein said stop means comprises a disc-shaped member whose major surface extends substantially parallel to said major arms when the latter are fully extended.

9. Endoscope according to claim 1 having at least four hook elements.

10. Endoscope for introduction through a body structure and into a hollow organ of a living thing, comprising a hollow outer shaft having a proximal region and a distal end, an optical system arranged in the shaft, a plurality of rigid, L-shaped hook elements linked to be radially pivotable at the distal end of the outer shaft, an axially movable inner shaft which accommodates the optical system and is guided on the outer shaft being provided to pivot the hook elements, adjustable and fixable stop means being arranged on the outer shaft, adjusting means provided in the proximal region of the outer shaft for displacing the inner shaft, and indicator means for reading the position of the adjusting means, each of said L-shaped hook elements having a major arm extending radially outwardly from said outer shaft when said hook elements are radially pivoted at the distal end, such that said major arms when fully extended cooperate with said stop means to pull and hold a hollow organ against a body structure between said arms and said stop means.

11. Endoscope according to claim 10, wherein the indicator means comprises a measuring scale provided on the outer shaft.

12. Endoscope according to claim 10 wherein said major arms, when fully extended, extend substantially perpendicular to the longitudinal axis of said shaft.

13. Endoscope according to claim 10 wherein said stop means comprises a disc-shaped member whose major surface extends substantially parallel to said major arms when the latter are fully extended.

14. Endoscope according to claim 10 having at least four hook elements.

* * * * *